United States Patent

Eliasson et al.

[11] Patent Number: 6,136,278
[45] Date of Patent: Oct. 24, 2000

[54] DISCHARGE REACTOR AND USES THEREOF

[75] Inventors: Baldur Eliasson, Birmenstorf; Ulrich Kogelschatz, Hausen, both of Switzerland

[73] Assignee: ABB Research Ltd., Zurich, Switzerland

[21] Appl. No.: 09/144,971

[22] Filed: Sep. 1, 1998

[30] Foreign Application Priority Data

Sep. 8, 1997 [DE] Germany ............................ 197 39 181

[51] Int. Cl.[7] ...................................................... B01J 19/08
[52] U.S. Cl. ................................ 422/186.04; 422/186.07
[58] Field of Search ........................ 204/176; 422/186.04, 422/186.07

[56] References Cited

U.S. PATENT DOCUMENTS

| | | | |
|---|---|---|---|
| 3,970,567 | 7/1976 | Lowther | 204/176 |
| 4,650,648 | 3/1987 | Beer et al. | 422/186.07 |
| 5,254,231 | 10/1993 | Heath et al. | |

FOREIGN PATENT DOCUMENTS

| | | |
|---|---|---|
| 0547366B1 | 6/1993 | European Pat. Off. . |
| 2413558 | 10/1974 | Germany . |
| 2519526 | 11/1975 | Germany . |
| 3605715A1 | 9/1986 | Germany . |
| 3220018C2 | 9/1990 | Germany . |
| 42 20 865 A1 | 2/1993 | Germany . |
| 4220865A1 | 2/1993 | Germany . |
| 19518970C1 | 11/1996 | Germany . |
| 1-103903 | 4/1989 | Japan . |
| 89-161591 | 4/1989 | Japan . |
| 08038881 | 2/1996 | Japan . |
| 96-233086 | 2/1996 | Japan . |

OTHER PUBLICATIONS

Perry & Chilton: Chemical Engineers' Handbook, 5th ed., 1973 McGraw–Hill, Inc., pp. 5–54.

"Greenhouse Gas Chemistry", Bill, et al., Energy Convers. Mgmt., vol. 38, 1997, pp. S415–S422 No Month Available.

Handbook of Electrostatic Processes, Chang, et al., 1995, pp. 581–605 No Month Available.

"Nonequilibrium Volume Plasma Chemical Processing", Eliasson, et al., IEEE Transactions on Plasma Science, vol. 19, No. 6, Dec. 1991, pp. 1063–1077.

*Primary Examiner*—Kathryn Gorgos
*Assistant Examiner*—Thao Tran
*Attorney, Agent, or Firm*—Burns, Doane, Swecker & Mathis, L.L.P.

[57] ABSTRACT

In an electrical discharge reactor for facilitating chemical reactions, power consumption and yield of chemical reactions are optimized, and heat dissipation is improved, by filling an interspace between a first electrode (1) and a second electrode (2) of the discharge reactor with a block (4) of rigid, open-pored dielectric material. The material preferably has a porosity of 80–90%. The skeleton of the block can consist of glass, quartz or ceramic. The diameter of the pores in the block, in which micro-discharges occur, represents an effective gap width that is critical for the progress of the silent discharge. The diameter of the pores can, for example, be between 0.05 millimeters and 0.2 millimeters to optimize power consumption. As a safeguard against breakdown, a barrier layer (5) of a nonconductive, solid material can be provided between the electrodes (1, 2). To facilitate a reaction of $CO_2$ and $H_2$ to form methanol and water, or to facilitate a reaction of $CO_2$ and $CH_4$ to form synthesis gas, the skeleton of the block can be coated with a suitable catalyst. The catalyst can include, for example, Cu and $ZrO_2$, or Cu and ZnO, or nickel compounds.

10 Claims, 2 Drawing Sheets

DISCHARGE REACTOR AND USES THEREOF

BACKGROUND OF THE INVENTION

1. Field of the Invention

The invention relates to a discharge reactor and uses thereof. Known generic discharge reactors for silent discharges and similar processes have, between two electrodes, at least one dielectric and a gas-containing discharge gap and are connected, usually in a plurality and in parallel, to an alternating voltage source. During each halfwave, microdischarges are ignited in the gap, breakdowns limited by the dielectric, which generate free radicals and thereby trigger specific chemical reactions in the gas.

2. Discussion of Background

General information on silent discharges and their uses may be obtained, for example, from the following publications: U. Kogelschatz: "Silent Discharges and their Applications" in: "Proceedings of the Tenth International Conference on Gas Discharges and their Applications", Vol. II, Swansea 1992 and B. Eliasson, U. Kogelschatz: "Nonequilibrium Volume Plasma Chemical Processing", IEEE Transactions on Plasma Science 19/6 page 1063–1077 (1991).

Discharge reactors have long been used to produce ozone from $O_2$ or air for the treatment of drinking water and other purposes. In addition to the abovementioned publications, reference is made, in this respect, to U. Kogelschatz, B. Eliasson: "Ozone Generation and Applications" in J.-S. Chang, A. J. Kelly, J. M. Crowley: "Handbook of Electrostatic Processes", Marcel Dekker, Inc. (1995), and to DE-C-32 20 018.

Another application, which is very useful in light of the increasingly urgent reduction in the emission of greenhouse gases, is the reaction of $CO_2$ and $H_2$ in methanol and water, see A. Bill, A. Wokaun, B. Eliasson, E. Killer, U. Kogelschatz: "Greenhouse Gas Chemistry", Energy Convers. Mgmt. 38, Suppl., page 415–422 (1997), and J. U. Höltje: "Untersuchung der Makrokinetic der heterogen katalysierten Synthese aus Kohlendioxid und Wasserstoff zu Methanol", ["Investigation of the macrokinetics of the heterogeneously catalyzed synthesis of carbon dioxide and hydrogen into methanol"], dissertation, Rheinisch-Westfälische Technische Hochschule, [Technical University of Rhine-Westphalia], Aachen 1991. The joint reaction of the greenhouse gases $CO_2$ and $CH_4$ into synthesis gas or syngas, a mixture of CO and $H_2$, is also important in this connection.

Other applications are the decomposition of pollution gases, for example in smoke gases from garbage incineration plants, but also in the exhaust gases of automobiles (see DE-C-195 18 970), and excimer lamps delivering UV radiation which is in a narrow frequency band and which is generated during the decay of excited states of inert gas atoms (see, for example, EP-B-0 547,366).

Various types of discharge reactors are known. Thus, the electrodes may be designed, for example, as parallel plates, or as concentric tubes. Without exception, an appropriately shaped dielectric is used, which separates the electrodes continuously and which consists of at least one layer of solid nonconductive material, for example glass. Said layer may be arranged directly on an electrode or else be spaced from the two electrodes. It is also possible to arrange two layers of this type so as preferably to adjoin the electrodes in each case. In the space between the electrodes there is, in each case, at least one discharge gap, into which the gaseous educts of the desired chemical reaction are introduced and in which microdischarges are formed under the influence of the electric field built up between the electrodes, said microdischarges producing highly reactive intermediate products, namely free electrons and radicals, of which the reactions with one another and, above all, with gas molecules or gas atoms result in the desired products with a yield which depends on various boundary conditions.

The supply voltage applied between the electrodes may correspond to the power supply frequency, as in early ozone generating plants, but, in modern plants, the frequency is usually substantially higher with a view to as high a yield as possible and may enter the GHz range.

The power consumption P of the gas during the silent discharge conforms to the law $$P = 4fC_D U_B(\hat{U} - (1-\beta)U_B), \quad (1)$$

f being the frequency of the supply voltage, $\hat{U}$ its amplitude, $C_D$ the capacitance of the dielectric, $U_B$ the mean drop voltage of the microdischarges, and $$\beta = C_S / C_D \quad (2)$$

being the quotient from the capacitance $C_S$ of the discharge gap and the capacitance $C_D$ of the dielectric.

Thus, in the case of fixed values for the frequency f, the amplitude $\hat{U}$ and the capacitance of the dielectric $C_D$, power consumption depends on $U_B$ and $\beta$ which, in turn, depend on the gap width of the discharge gap d. In the case of the boundary conditions which are otherwise given (gas composition, pressure and temperature in the discharge gap), the power consumption P and, together with it, the yield of the discharge reactor can therefore be optimized by adjusting this variable.

In actual fact, however, the optimal width of the discharge gap is usually so small that, in the case of discharge reactors which are sufficiently high-performance for economic production and correspondingly large, production tolerances place limits on the gap setting and the actual gap width is to a greater or lesser extent above the optimum.

It is known, admittedly, to fill the discharge gap with a material which occupies part of the volume and leaves free an interconnected branched gas volume. Thus, heaps of particles consisting, for example, of ceramic, said particles filling the discharge gap, are described for generic or similar reactors in JP-A-103 903/89, JP-A-038 881/96, JP-A-261 034/89 and U.S. Pat. No. 5,254,231. In heaps of this kind, however, cavities of widely varying and hardly controllable size occur and the porosity as a whole is low, so that the volume is utilized poorly and flow resistance for the gas flowing through is high. The granulates are also difficult to handle and their properties may easily be impaired by mechanical actions.

DE-A-42 20 865 discloses a generic discharge reactor, in which the discharge gap is filled with glass wool, quartz wool or mineral wool. However, these materials likewise leave free cavities of varying extent which is difficult to control. The discharge gap can be filled up completely only with difficulty on account of their mechanical properties. The same publication also mentions the possibility of applying a porous layer to one of the electrodes. However, this is merely a relatively thin layer consisting of a catalyst material or of a carrier material for the latter, said material taking up only a small part of the discharge gap.

SUMMARY OF THE INVENTION

Accordingly, one object of the invention is to provide a novel generic discharge reactor of improved efficiency, which is simple to produce and is mechanically stable.

The invention provides a discharge reactor, in which small effective gap widths can be readily achieved, even in the case of large dimensions, the porous material used dividing the discharge gap in a stable manner into a multiplicity of relatively well-defined volumes, namely the individual pores, in which microdischarges essentially independent of one another are formed in each case, so that the effective gap width d critical for the progress of the silent discharge corresponds to the clear width of the pores. In this way, a substantially higher power consumption can be achieved and the yield markedly improved. The porosity can be selected very high, thus improving efficiency and reducing flow resistance.

However, the design according to the invention of generic discharge reactors also has other advantages. Thus, the dissipation of the heat generated by the microdischarges out of the discharge gap by heat conduction via the skeleton of the open-pored material is substantially more effective than dissipation via gas or via known materials used for filling up the discharge gap. It is therefore substantially easier to maintain the gas at an approximately optimal temperature.

Moreover, a large surface is available, which may be utilized for triggering the desired chemical reaction, or improving its yield, by coating or packing the skeleton with a suitable catalyst.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
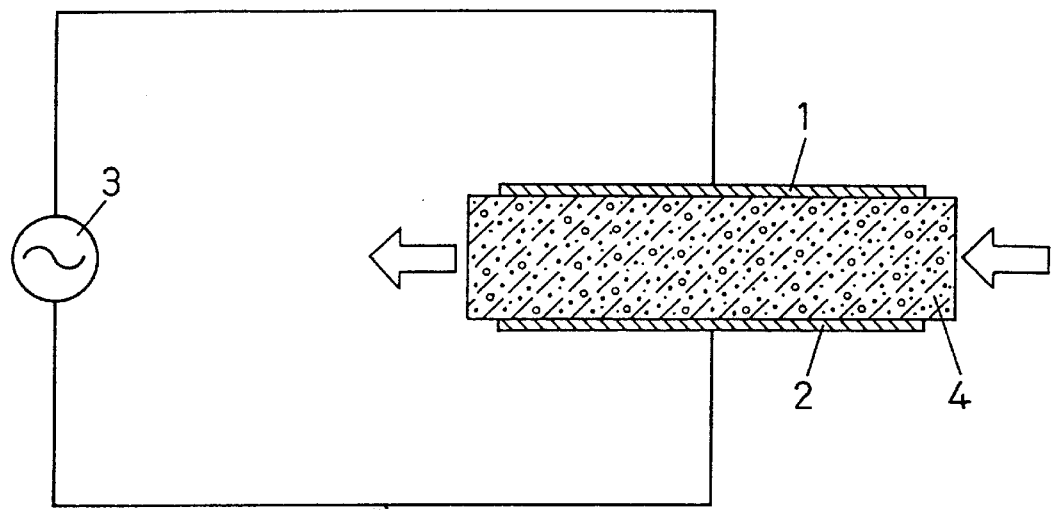
FIG. 1 shows a diagrammatic illustration of a discharge reactor according to the invention in a first embodiment.

Referring now to the drawings, wherein like reference numerals designate identical or corresponding parts throughout the several views, the discharge reactor has, in each case, a first electrode 1 and a second electrode 2, to which a supply voltage source 3 is applied. The electrodes 1, 2 may have various geometric shapes. In particular, they may be designed as parallel spaced plates or as preferably concentrically arranged tubes. The latter configuration, above all, is preferably selected, a multiplicity of discharge reactors then being combined in parallel, and also connected electrically in parallel, to form a battery of honeycomblike structure, through which cooling water flows between the reactors. A high production capacity can be achieved in a small space by means of an arrangement of this type.

The supply voltage source 3 delivers an alternating voltage, the frequency of which may be between a few Hz and a few GHz. Since, according to (1), the power consumption of the discharge reactor is, within certain limits, proportional to the frequency, in general high frequencies in the MHz range or even GHz range are preferred today with a view to a high yield. The amplitude must be such that the ignition voltage reached in the discharge gap and microdischarges are triggered during each halfwave.

In the discharge reactor according to the first embodiment (FIG. 1), the gap located between the first electrode 1 and the second electrode 2 is filled up completely by a layer consisting of a filler, namely a rigid open-pored material which also acts as a dielectric limiting the microdischarges. The rigid open-pored material is arranged in the form of a solid block 4 between the electrodes.

A gas stream (arrows) is conducted through between the electrodes 1, 2, the desired chemical reactions being triggered in said gas stream by the silent discharge taking place in the pores of the block 4. The gas drawn off from the discharge gap can then be processed further by means of physical or chemical methods, and, for example, the desired products can be isolated. The chemical reactions may, under some circumstances, be assisted, or even made possible for the first time, by catalysts in the block 4. Instead of being led parallel to the electrodes, the gas stream may also be led through the electrodes which then, of course, must be designed so as to be permeable to gas, for example as porous sintered plates or perforated metal diaphragms or plates.

Figure 2:
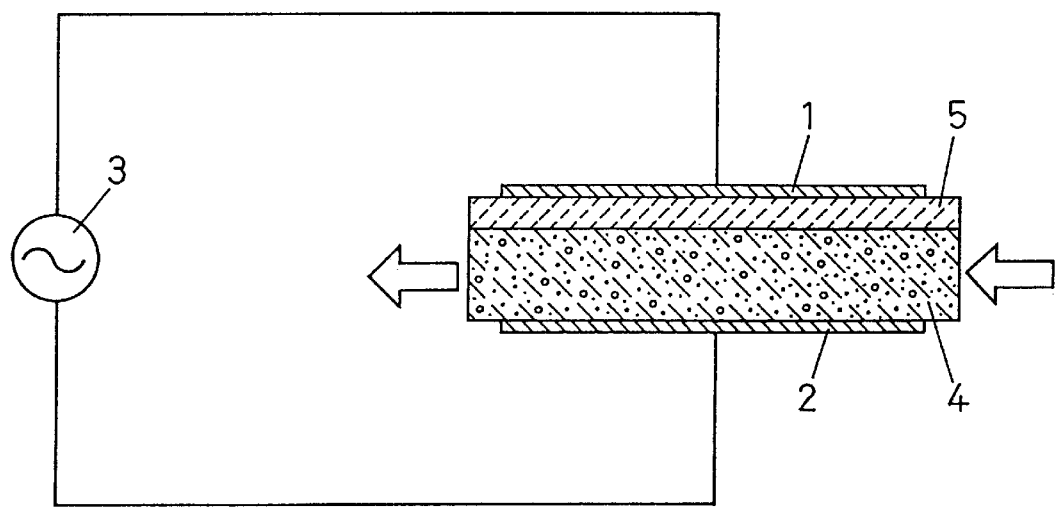
FIG. 2 shows a diagrammatic illustration of a discharge reactor according to the invention in a second embodiment.

Although the block 4 is, as a rule, sufficient as protection against breakdowns, it is possible, as a safeguard in this respect, to reinforce the dielectric by means of a barrier layer 5 arranged continuously between the electrodes 1, 2 and consisting of solid material, as illustrated in the second embodiment according to FIG. 2. This may, for example, be glass, quartz, ceramic or another suitable nonconductive material. The layer may be arranged directly on one of the electrodes, for example on the first electrode 1, as illustrated, or else so as to be spaced from both electrodes.

Figure 3:
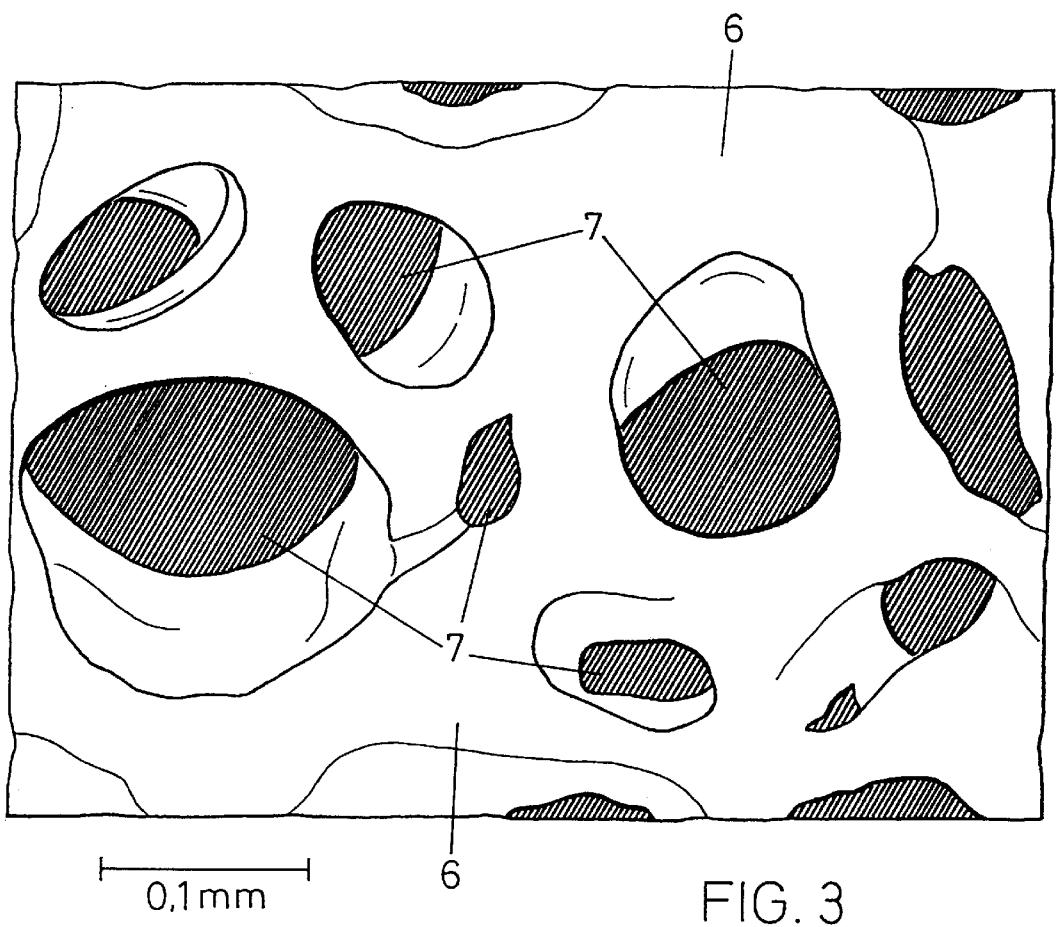
FIG. 3 shows the surface of a block of open-pored material suitable for use in discharge reactors according to the invention.

The rigid open-pored material of the block 4 has a solid skeleton 6 (FIG. 3) which divides the volume of the discharge gap into a multiplicity of open interconnected pores 7. The skeleton must consist of nonconductive material which is resistant to microdischarges and is chemically inert. In the latter respect, the specific requirements depend on the area of use. As may be gathered from what was discussed further above in connection with the power consumption in the discharge gap, the optimal pore size depends on the geometric and electric boundary conditions. As a rule, it should be of the order of magnitude of 0.1 mm, for example between 0.05 mm and 0.2 mm. A large reaction volume, that is to say a high porosity of at least 50%, preferably 80–90% or above, and a high dielectric constant, which may, for example, be between 3 and 20, are also beneficial with a view to a high yield. The desired stabilization of the gas temperature is assisted by high thermal conductivity and heat capacity.

These requirements are satisfied by various known materials, in particular by porous glass and porous quartz which, due to its UV permeability, is also suitable for use in excimer lamps. Porous ceramic, such as is offered by the company Bridgestone under the designation Ceramic Foam is also highly advantageous (Ceramic Foam, Technical Report No. 1). This material is distinguished by high porosity (80–90%), low specific gravity, high heat resistance (up to 1150° C.) and chemical resistance. Moreover, the pressure drop of the gas stream is relatively slight. It is also possible to use porous ceramic sintered material.

All the materials mentioned are mechanically highly stable, in particular their properties important for their function are robust in respect of mechanical loads. The pore size is, as a rule, well-defined and fluctuates relatively little.

Discharge reactors according to the invention are suitable, in practice, for all known uses of known generic reactors. In this case, in particular, mention may be made of ozone generation and the generation of methanol from $CO_2$ and $H_2$ and of synthesis gas (CO and $H_2$) from $CO_2$ and $CH_4$. In order to generate methanol, $CO_2$ and $H_2$ are conducted through the discharge reactor and reacted under the effect of the silent discharge in order, in part, to form methanol and water. $Cu/ZrO_2$ or $Cu/ZnO$ catalysts are used in this reaction. In the otherwise similar generation of synthesis gas, for example nickel compounds may serve as catalysts.

In the discharge reactor according to the invention, then, the skeleton 6 of the block 4 may be coated or packed with catalyst material. For the coating, for example solid copper and zinc compounds, etc. may be dissolved in a solvent, then evaporated together with the latter and precipitated out of the gas phase on the walls of the pores 7. Precipitation directly from gaseous metalloorganic compounds is also possible. Precipitation may be triggered by raising the temperature or, if appropriate, additionally by igniting a silent discharge. This may then be followed by an oxidation step, in which the material of the block 4 is exposed to air or oxygen, and conditioning in a hydrogenous atmosphere. In these steps, too, temperature treatment and silent discharge may be employed.

Obviously, numerous modifications and variations of the present invention are possible in the light of the above teachings. It is therefore to be understood that, within the scope of the appended claims, the invention may be practiced otherwise than as specifically described herein.

What is claimed is:

1. A discharge reactor with at least first and second electrodes spaced apart with a discharge gap which is located between the at least first and second electrodes and which is filled up by a filler comprising at least one block of rigid, porous dielectric material forming a network of interconnected cavities, the at least one block having a porosity between at least 50% and 95%.

2. The discharge reactor as claimed in claim 1, wherein a diameter of the pores of the block is between 0.05 millimeters and 0.2 millimeters.

3. The discharge reactor as claimed in claim 1, wherein a material of a skeleton of the block has a dielectric constant of at least 3.

4. The discharge reactor as claimed in claim 1, wherein a skeleton of the block consists of ceramic, glass or quartz.

5. The discharge reactor as claimed in claim 1, wherein the filler further comprises at least one barrier layer consisting of solid material.

6. The discharge reactor as claimed in claim 1, wherein a skeleton of the block is coated or packed with a catalyst material.

7. The discharge reactor as claimed in claim 6, wherein the catalyst material contains at least one metal compound.

8. The discharge reactor as claimed in claim 6, wherein the catalyst material contains Cu and $ZrO_2$ or Cu and ZnO.

9. The discharge reactor as claimed in claim 6, wherein the catalyst material contains at least one nickel compound.

10. The discharge reactor as claimed in claim 1, wherein the porosity of the at least one block is between 80% and 90%.

* * * * *